(12) United States Patent
Lin et al.

(10) Patent No.: US 9,359,293 B2
(45) Date of Patent: Jun. 7, 2016

(54) METHODS OF TREATMENT USING MODULATORS OF SIRT2

(71) Applicant: CORNELL UNIVERSITY, Ithaca, NY (US)

(72) Inventors: Hening Lin, Ithaca, NY (US); Bin He, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/349,140

(22) PCT Filed: Oct. 5, 2012

(86) PCT No.: PCT/US2012/058846
§ 371 (c)(1),
(2) Date: Apr. 2, 2014

(87) PCT Pub. No.: WO2013/052727
PCT Pub. Date: Apr. 11, 2013

(65) Prior Publication Data
US 2014/0249216 A1    Sep. 4, 2014

Related U.S. Application Data

(60) Provisional application No. 61/544,452, filed on Oct. 7, 2011.

(51) Int. Cl.
*C07C 327/42*    (2006.01)
*A61K 31/16*    (2006.01)

(52) U.S. Cl.
CPC ............... *C07C 327/42* (2013.01); *A61K 31/16* (2013.01)

(58) Field of Classification Search
CPC ..................................................... C07C 327/42
See application file for complete search history.

(56) References Cited

U.S. PATENT DOCUMENTS

| 2005/0137230 A1 | 6/2005 | Dorsch et al. |
| 2007/0021434 A1 | 1/2007 | Boyd et al. |
| 2007/0142638 A1 | 6/2007 | Hattori et al. |
| 2008/0171783 A1 | 7/2008 | Cameron et al. |

FOREIGN PATENT DOCUMENTS

CN    1898227 A    1/2007

OTHER PUBLICATIONS

Outeiro et al. Science 2007, 317, 516-519.*
Gal et al. Neurochem. Int. 2012, 61, 992-1000.*
McGlynn et al. European Journal of Cancer 2014, 50, 290-301.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) pp. 427-431.*
Kamb, Nature Reviews Drug Discovery 4, 161-165 (Feb. 2005).*
Luo et al. Cell 2009, 136, 823-837.*
Roberts, Jr. et al., JAMA 292(17): 2130-2140 (2004).*
Kola, Nature Reviews Drug Discovery 3, 711-715 (2004).*
Haigis M.C. et al., "Mammalian Sirtuins: Biological Insights and Disease Relevance", Annu. Rev. Pathol. Mech. Dis 5:253-295 (2010).
Heltweg B. et al., "Antitumor Activity of a Small-Molecule Inhibitor of Human Silent Information Regulator 2 Enzymes", Cancer Res 66(8):4368-4377 (Apr. 15, 2006).
Imai S-I et al., "Ten Years of Nad-Dependent SIR2 Family Deacetylases: Implications for Metabolic Diseases", Trends in Pharmacological Sciences 31(5):212-220 (2010).
Jiang W. et al., "Acetylation Regulates Gluconeogenesis by Promoting PEPCK1 Degradation Via Recruiting the UBR5 Ubiquitin Ligase", Molecular Cell 43:33-44 (Jul. 8, 2011).
Luthi-Carter R. et al., "SIRT2 Inhibition Achieves Neuroprotection by Decreasing Sterol Biosynthesis", PNAS 107 (17):7927-7932 (Apr. 27, 2010).
Machado De Oliveira R. et al., "SIRT2 as a Therapeutic Target for Age-Related Disorders", Frontiers in Pharmacology 3, Article 82:1-9 (May 2012).
Michishita E et al., "Evolutionarily Conserved and Nonconserved Cellular Localizations and Functions of Human SIRT Proteins", Molecular Biology of the Cell 16:4623-4635 (Oct. 2005).
North B.J. et al., "The Human Sir2 Ortholog, SIRT2, is an NAD+-Dependent Tubulin Deacetylase", Molecular Cell 11:437-444 (Feb. 2003).
Suzuki T. et al., "Identification of a Cell-Active Non-Peptide Sirtuin Inhibitor Containing N-Thioacetyl Lysine", Bioorganic & Medicinal Chemistry Letters 19:5670-5672 (2009).
Zhang Y. et al., "Identification of a Small Molecule SIRT2 Inhibitor With Selective Tumor Cytotoxicity", Biochemical and Biophysical Research Communications 386:729-733 (2009).
International Search Report dated Feb. 14, 2013 received from the Russian Patent Office from related International Application No. PCT/US2012/058846.
Chinese Office Action dated Feb. 13, 2015 received from Application No. 201280059788.2, together with an English-language translation.
European Extended Supplementary Search Report dated Jul. 20, 2015 received from Application No. 12838058.1.

* cited by examiner

*Primary Examiner* — Matthew Coughlin
(74) *Attorney, Agent, or Firm* — Scully, Scott, Murphy & Presser, P.C.

(57) ABSTRACT

The instant application describes novel compounds that modulate (in particular, inhibit) Sirt2 , with structures according to Formulas (1) and (2) provided herein. The invention is also directed to pharmaceutical compositions thereof, methods of treatment (i.e., cancer and neurodegenerative disease) by administration of the modulating compounds, assay methods for finding modulators of Sirt2 , and kits for practicing the assay method.

26 Claims, 5 Drawing Sheets

(3A)

(3B)

METHODS OF TREATMENT USING MODULATORS OF SIRT2

CROSS-REFERENCE TO RELATED APPLICATIONS

This application claims priority from U.S. Provisional Application No. 61/544,452, filed Oct. 7, 2011, which is herein incorporated by reference in its entirety.

STATEMENT REGARDING FEDERALLY SPONSORED RESEARCH

This invention was made with government support under Contract No. GM086703 awarded by the National Institutes of Health. The government has certain rights in the invention.

BACKGROUND OF THE DISCLOSURE

Sirtuins are a class of enzymes known as nicotinamide adenine dinucleotide (NAD)-dependent deacetylases. Humans have seven sirtuins, Sirt1-7, that regulate a variety of biological processes, including aging, transcription, and metabolism. Therefore, small molecules that can regulate sirtuin activity can be used to treat several human diseases.

Several proteins (such as epidermal growth factor receptor 2 or HER2 for breast cancer treatment, BCR-ABL for chronic myeloid leukemia treatment) have been used as pharmacological targets for treating human cancers. However, due to the heterogeneity of cancer and the occurrence of drug resistance, there is an ongoing need for the identification of new protein targets and new pharmacological reagents for treating cancer.

Sirt2 is one of the seven members of the Sir2-family of NAD+-dependent deacetylases (or sirtuins) in humans. A general schematic of the process by which sirtuins catalyze NAD-dependent protein lysine deacetylation is shown in FIG. 1. Sirtuins have been conserved through evolution and have been implicated in a number of biological functions, perhaps foremost being the regulation of lifespan (e.g., Haigis, M. C., et al., *Annu. Rev. Pathol.* 5, 253-295, 2010; and Imai, S.-i., et al., *Trends in Pharmacological Sciences* 31, 212-220, 2010). Among the seven mammalian sirtuins, Sirt2 is the only cytosolic one (e.g., Michishita, E., et al., *Mol. Biol. Cell* 16, 4623-4635, 2005). Two cytosolic Sirt2 substrates have been identified and confirmed in cellular studies, α-tubulin and phosphoenolpyruvate carboxykinase (PEPCK) (e.g., North, B. J., et al., *Mol. Cell* 11, 437-444, 2003; Jiang, W., et al., *Mol. Cell* 43, 33-44, 2011). Sirt2 destabilizes microtubules by deacetylating α-tubulin Lys40. By deacetylating PEPCK and regulating PEPCK stability, Sirt2 also regulates gluconeogenesis.

The anti-cancer effects of small-molecule inhibitors of Sirt2 have been described, e.g., Heltweg, B., et al., *Cancer Res.* 66, 4368-4377, 2006; Zhang, Y., et al., *Biochem. Biophys. Res. Commun.* 386, 729-733, 2009. However, the known inhibitors generally have higher than optimal $IC_{50}$ values against Sirt2, and also lack specificity against Sirt2. Moreover, attaining such specificity against Sirt2 could provide significant advantages for the treatment of particular types of cancer, such as breast cancer, and more particularly, triple negative breast cancer. Sirt2 has also been shown to be involved in neurodegenerative disease (e.g., Luthi-Carter, R., et al., *Proc. Natl. Acad. Sci. USA*, 107(17):7927-32, Apr. 27, 2010, and de Oliveira, R. M., et al., *Front Pharmacol.*, 3:82, 2012). Thus, such inhibitors against Sirt2 could also provide an improved treatment of neurodegenerative disease.

BRIEF SUMMARY OF THE DISCLOSURE

In this application, novel modulators are described that have improved and even selective activity against human Sirt2 protein. These modulators are useful in the treatment of, for example, cancer, such as breast cancer, and neurodegenerative disease.

In particular embodiments, the modulators considered herein have the following chemical structure:

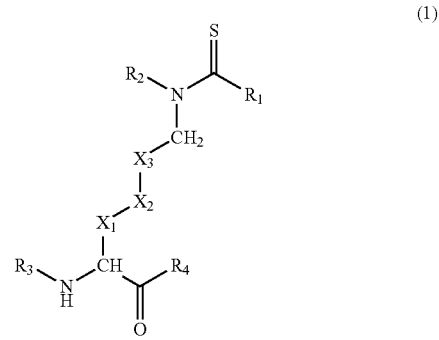

(1)

In Formula (1), $R_1$ is a hydrocarbon group having at least five carbon atoms connected by carbon-carbon bonds, wherein the hydrocarbon group optionally includes one heteroatom group selected from —O—, —$NR_5$—, and —S— that interrupts a carbon-carbon bond of the hydrocarbon group, and wherein one or more hydrogen atoms in the hydrocarbon group are optionally replaced with fluoro atoms, wherein $R_5$ is a hydrogen atom or a hydrocarbon group. The group $R_2$ is selected from a hydrogen atom or a hydrocarbon group. The groups $R_3$ and $R_4$ are independently selected from hydrogen atom and hydrocarbon groups R, wherein the hydrocarbon groups R are optionally substituted with one or more heteroatoms. The linking moieties $X_1$, $X_2$, and $X_3$ are independently selected from —$(CH_2)_n$—, —$NR_5$—, —O—, —S—, or a bond, wherein n represents 1, 2, or 3, and at least one of $X_1$, $X_2$, and $X_3$ is a —$CH_2$ group.

In particular embodiments of Formula (1), the modulators considered herein have the following chemical structure:

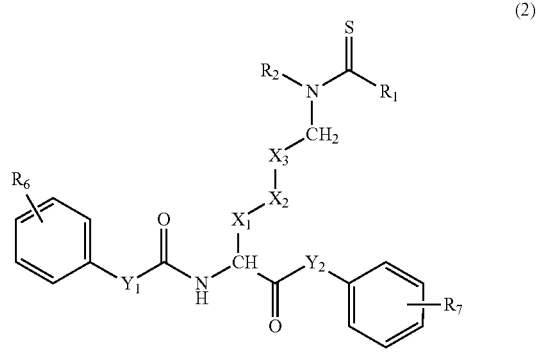

(2)

In Formula (2), the groups $R_1$, $R_2$, $X_1$, $X_2$, and $X_3$ are as described above under Formula (1). The groups $R_6$ and $R_7$ are independently selected from hydrogen atom, unsubstituted hydrocarbon groups having up to six carbon atoms, alkoxy groups —OR, amide groups —NR'C(O)R or —C(O)NR'R, ketone groups —C(O)R, ester groups —C(O)OR or —OC(O)R, carbamate groups —OC(O)NR'R or —NR'C(O)OR, and urea groups —NR'C(O)NRR', wherein R is a hydrocarbon group having up to six carbon atoms, and R' is a hydrogen atom or a hydrocarbon group having up to six carbon atoms. The linking moieties $Y_1$ and $Y_2$ are independently selected from —O—, —$NR_5$—, and —S— groups.

The invention is also directed to a method for treating a subject afflicted with a disorder treatable by modulating Sirt2 activity. In the method, a subject afflicted with such a disorder, particularly cancer (e.g., breast cancer) or a neurodegenerative disorder (e.g., Parkinson's, Huntington's, or Alzheimer's) is administered a modulating compound described above in a pharmaceutically effective amount for treating the disorder. The invention is also directed to assay methods for identifying a modulating compound of Sirt2, as well as a kit for practicing the assay method.

DETAILED DESCRIPTION OF THE DISCLOSURE

Figure 1:
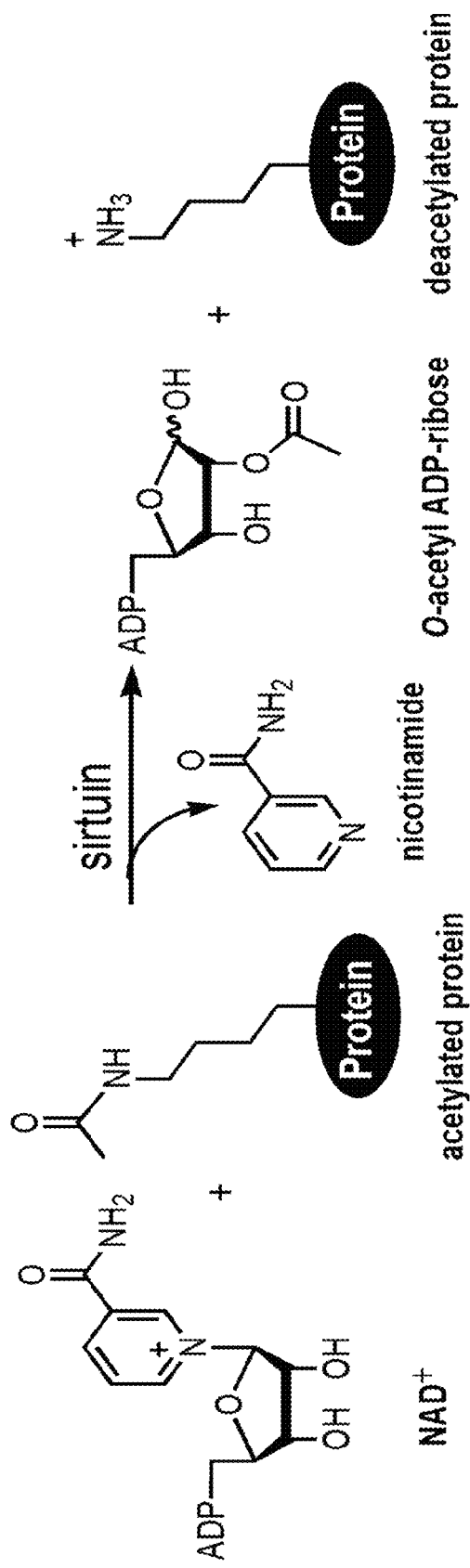
FIG. 1. General schematic showing the process by which sirtuins catalyze NAD-dependent protein lysine deacetylation.

For convenience, before further description of the present invention, certain terms employed in the specification, examples, and appended claims are described. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. In some embodiments, the term "amino acid" refers only to the twenty known essential amino acids, or a subset thereof, i.e., glycine (G), alanine (A), valine (V), leucine (L), isoleucine (I), cysteine (C), methionine (M), phenylalanine (F), tyrosine (Y), tryptophan (W), proline (P), serine (S), threonine (T), asparagine (N), glutamine (Q), aspartic acid (D), glutamic acid (E), histidine (H), lysine (K), and arginine (R). In some embodiments, one or more of any of the foregoing classes or specific types of amino acids are excluded.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing. They may include one or more types of any of the amino acid residues described above, or a modified form thereof, and typically include at least 10, 20, 30, 40, or 50, and up to 80, 100, 120, 150, 200, 300, 400, 500, or 1,000 amino acid residues. The term "oligopeptide", as used herein, generally refers to a chain of amino acid residues of at least 4, 5, or 6 and up to 8, 10, 15, or 20. The terms "dipeptide" and "tripeptide" refer, respectively, to two and three linked amino acid residues.

The term "high throughput screening" (HTS) refers to an automated, large-scale method to test small molecule inhibitors for inhibition of a particular enzyme activity or cellular process. HTS typically tests a library of different compounds to determine their activities.

As used herein, the term "modulator" includes any substance that activates or inhibits Sirt2 deacylase activity. Moreover, an "activator" is a substance that increases, enhances, or accelerates Sirt2 deacylase activity, while an "inhibitor" is a substance that reduces, inhibits, or prevents Sirt2 deacylase activity.

The terms "hydrocarbon group", i.e., "hydrocarbon group (R)", and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, twenty, twenty-one, twenty-two, or twenty-three carbon atoms, or a number of carbon atoms within a particular range bounded by any two of the foregoing carbon numbers. Hydrocarbon groups or linkers in different compounds described herein, or in different positions of a compound, may possess the same or different number (or preferred range thereof) of carbon atoms in order to independently adjust or optimize the activity or other characteristics of the compound.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene linker, i.e., —$CH_2$—, or methine linker), ethyl (or ethylene or dimethylene linker, i.e., —$CH_2CH_2$— linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, 3-methylpentyl, and the numerous $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, and $C_{23}$ saturated and branched hydrocarbon groups. Some examples of branched alkylene linkers are those derived by removal of a hydrogen atom from one of the foregoing exemplary branched alkyl groups (e.g., isopropylene, —CH(CH$_3$)CH$_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl (CH$_2$=CH—CH$_2$—CH$_2$—), 2-buten-1-yl (CH$_2$—CH=CH—CH$_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous C$_7$, C$_8$, C$_9$, C$_{10}$, C$_{11}$, C$_{12}$, and higher unsaturated and straight-chained hydrocarbon groups. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers can alternatively be unsaturated and branched (i.e., branched olefinic or alkenyl groups or linkers). Some examples of branched olefinic groups include propen-2-yl, 3-buten-2-yl (CH$_2$=CH—CH.—CH$_3$), 3-buten-3-yl (CH$_2$=C.—CH$_2$—CH$_3$), 4-penten-2-yl, 4-penten-3-yl, 3-penten-2-yl, 3-penten-3-yl, 2,4-pentadien-3-yl, and the numerous C$_6$, C$_7$, C$_8$, C$_9$, C$_{10}$, C$_{11}$, C$_{12}$, and higher unsaturated and branched hydrocarbon groups. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers may also include one or more heteroatoms (i.e., non-carbon and non-hydrogen atoms), such as one or more heteroatoms selected from oxygen (O), nitrogen (N), sulfur (S), phosphorus (P), and halide atoms, as well as groups containing one or more of these heteroatoms (i.e., heteroatom-containing groups). Some examples of oxygen-containing groups include hydroxy (OH), carbonyl-containing (e.g., carboxylic acid, ketone, aldehyde, carboxylic ester, amide, and urea functionalities), nitro (NO$_2$), carbon-oxygen-carbon (ether), sulfonyl, and sulfinyl (i.e., sulfoxide), and amine oxide groups. The ether group can also be a polyalkyleneoxide group, such as a polyethyleneoxide group. Some examples of nitrogen-containing groups include primary amine, secondary amine, tertiary amine, quaternary amine, cyanide (i.e., nitrile), amide (i.e., —C(O)NR$_2$ or —NRC(O), wherein R is independently selected from hydrogen atom and hydrocarbon group, as described above), nitro, urea, imino, and carbamate, wherein it is understood that a quaternary amine group necessarily possesses a positive charge and requires a counteranion. Some examples of sulfur-containing groups include mercapto (i.e., —SH), thioether (i.e., sulfide), disulfide, sulfoxide, sulfone, sulfonate, and sulfate groups. Some examples of phosphorus-containing groups include organophosphate, organophosphite and organophosphonate groups. Some examples of halide atoms considered herein include fluorine, chlorine, and bromine. One or more of the heteroatoms described above (e.g., oxygen, nitrogen, and/or sulfur atoms) can be inserted between carbon atoms (e.g., as —O—, —NR—, or —S—), or replace a carbon atom (or methylene group) in any of the hydrocarbon groups described above to form a heteroatom-substituted hydrocarbon group or linker. Alternatively, or in addition, one or more of the heteroatom-containing groups can replace one or more hydrogen atoms on the hydrocarbon group or linker.

In particular embodiments, the hydrocarbon group is, or includes, a cyclic or polycyclic group that includes at least one ring heteroatom (for example, one, two, three, four, or higher number of heteroatoms). Such ring heteroatom-substituted cyclic groups are referred to herein as "heterocyclic groups". As used herein, a "ring heteroatom" is an atom other than carbon and hydrogen (typically, selected from nitrogen, oxygen, and sulfur) that is inserted into, or replaces a ring carbon atom in, a hydrocarbon ring structure. In some embodiments, the heterocyclic group is saturated, while in other embodiments, the heterocyclic group is unsaturated (i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom). In some embodiments, the heterocyclic group is bound via one of its ring carbon atoms to another group (i.e., other than hydrogen atom and adjacent ring atoms), while the one or more ring heteroatoms are not bound to another group. In other embodiments, the heterocyclic group is bound via one of its heteroatoms to another group, while ring carbon atoms may or may not be bound to another group.

Some examples of saturated heterocyclic groups include those containing at least one oxygen atom (e.g., oxetane, tetrahydropyran, tetrahydropyran, 1,4-dioxane, 1,3-dioxane, and 1,3-dioxepane rings), those containing at least one nitrogen atom (e.g., pyrrolidine, piperidine, piperazine, imidazolidine, azepane, and decahydroquinoline rings), those containing at least one sulfur atom (e.g., tetrahydrothiophene, tetrahydrothiopyran, 1,4-dithiane, 1,3-dithiane, and 1,3-dithiolane rings), those containing at least one oxygen atom and at least one nitrogen atom (e.g., morpholine and oxazolidine rings), those containing at least one oxygen atom and at least one sulfur atom (e.g., 1,4-thioxane), and those containing at least one nitrogen atom and at least one sulfur atom (e.g., thiazolidine and thiamorpholine rings).

Some examples of unsaturated heterocyclic groups include those containing at least one oxygen atom (e.g., furan, pyran, 1,4-dioxin, and dibenzodioxin rings), those containing at least one nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings), those containing at least one sulfur atom (e.g., thiophene, thianaphthene, and benzothiophene rings), those containing at least one oxygen atom and at least one nitrogen atom (e.g., oxazole, isoxazole, benzoxazole, benzisoxazole, oxazoline, 1,2,5-oxadiazole (furazan), and 1,3,4-oxadiazole rings), and those containing at least one nitrogen atom and at least one sulfur atom (e.g., thiazole, isothiazole, benzothiazole, benzoisothiazole, thiazoline, and 1,3,4-thiadiazole rings).

In some embodiments, any of the generic substituents (e.g., R, $R_1$, $R_2$, and the like) described below may independently exclude any one or more of the classes, subclasses, or particular hydrocarbon groups described above, or may independently include only specific hydrocarbon groups selected from the hydrocarbon groups (R) described above.

The term "acyl" used herein refers to an organic group of the general formula —C(X)R, wherein X is oxygen (=O), sulfur (=S), or amino (=NR) and R independently represents a hydrocarbon group. For purposes of the instant invention, the hydrocarbon group R attached to C(X) possesses at least three carbon atoms connected by carbon-carbon bonds. In different embodiments, the hydrocarbon group R attached to C(X) possesses precisely or at least three, four, five, six, seven, eight, nine, ten, eleven, twelve, thirteen, fourteen, fifteen, sixteen, seventeen, eighteen, nineteen, or twenty carbon atoms, or a number of carbon atoms within a range bounded by any two of the foregoing number of carbon atoms (for example, a carbon number in the range of 3-20, 3-18, 3-16, 3-14, 3-12, 3-10, 3-8, 4-20, 4-18, 4-16, 4-14, 4-12, 4-10, 4-8, 5-20, 5-18, 5-16, 5-14, 5-12, 5-10, 5-8, 6-20, 6-18, 6-16, 6-14, 6-12, 6-10, 6-8, 7-20, 7-18, 7-16, 7-14, 7-12, 7-10, 8-20, 8-18, 8-16, 8-14, 8-12, 9-20, 9-18, 9-16, 9-14, 9-12, 10-20, 10-18, 10-16, 10-14, 10-12, 11-20, 11-18, 11-16, 11-14, 12-20, 12-18, 12-16, 12-14, 13-20, 13-18, 13-16, 14-20, 14-18, or 14-16 carbon atoms).

In one set of embodiments, the hydrocarbon group R attached to C(X) is composed of only carbon and hydrogen atoms. In another set of embodiments, the hydrocarbon group R attached to C(X) is composed of carbon and hydrogen atoms, wherein one or more hydrogen atoms may be substituted by one or more fluoro (F) atoms. In another set of embodiments, the hydrocarbon group R attached to C(X) is composed of carbon and hydrogen atoms, and optionally one or more fluoro atoms, along with one heteroatom selected from O, N, and S that either interrupts a carbon-carbon bond of the hydrocarbon group (R) or replaces a carbon atom (i.e., methylene or methine group) of the hydrocarbon group (R), except that the heteroatom is not included as an OH, SH, or $NH_2$ group, or any charged group, such as alkoxide, sulfide, carboxylate, or ammonium groups, since these types of groups would render the acyl portion too hydrophilic (i.e., not sufficiently hydrophobic). In some embodiments, the hydrocarbon group R attached to C(X) is selected from one or more of straight-chained or branched alkyl, alkenyl, or alkynyl, which may include or exclude one or more heteroatoms; cycloalkyl; aromatic ring; heterocycloalkyl; heteroaromatic; or a hydrocarbon group that includes any one or more of the foregoing substituent classes, such as an alkyl-aromatic, alkyl-heterocyclic, or alkyl-heteroaromatic group. When a heteroatom replaces a carbon atom, the possibility is included that the heteroatom is attached to the carbon of C(X), i.e., as C(X)—O—R, C(X)—S—R, C(X)—NH—R, or C(X)—NR—R, where each instance of an R group is an independent selection.

In particular embodiments, the modulators considered herein have the following chemical structure:

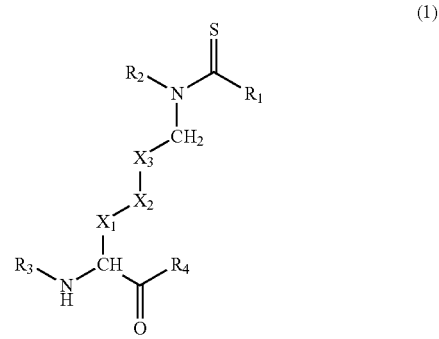

(1)

In Formula (1), $R_1$ is a hydrocarbon group having precisely or at least five, six, seven, eight, nine, ten, eleven, twelve, thirteen, fourteen, fifteen, sixteen, seventeen, eighteen, nineteen, twenty, twenty-one, twenty-two, or twenty-three carbon atoms connected by carbon-carbon bonds, wherein the hydrocarbon group optionally includes one heteroatom group selected from —O—, —$NR_5$—, and —S— that interrupts a carbon-carbon bond of the hydrocarbon group, and wherein one or more hydrogen atoms in the hydrocarbon group are optionally replaced with fluoro atoms. In some embodiments, $R_1$ has at least five, six, seven, eight, nine, ten, eleven, twelve, thirteen, fourteen, fifteen, or sixteen carbon atoms connected by carbon-carbon bonds in the absence of heteroatom substitution, except that that one or more hydrogen atoms may optionally be replaced with fluoro atoms. The group $R_5$ is typically a hydrogen atom or a hydrocarbon group, typically having up to one, two, three, four, five, or six carbon atoms. The group $R_2$ is also selected from a hydrogen atom or a hydrocarbon group, typically having up to one, two, three, four, five, or six carbon atoms. The groups $R_3$ and $R_4$ are independently selected from hydrogen atom and hydrocarbon groups R, wherein the hydrocarbon groups R are optionally substituted with one or more heteroatoms. The linking moieties $X_1$, $X_2$, and $X_3$ are independently selected from —$(CH_2)_n$—, —$NR_5$—, —O—, —S—, or a bond, wherein n represents 1, 2, or 3, and at least one of $X_1$, $X_2$, and $X_3$ is a —$CH_2$ group. In some embodiments, all of $X_1$, $X_2$, and $X_3$ are —$(CH_2)_n$— or $CH_2$ groups.

The groups $R_3$ and $R_4$ are independently hydrogen atom or any of the substituted or unsubstituted hydrocarbon groups R described above, or a selection thereof, wherein $R_4$ can alternatively be OH, $NH_2$, or SH. In some embodiments, one or both of $R_3$ and $R_4$ are non-biological (i.e. synthetic) groups containing at least 1, 2, 3, 4, or 5 and up to 10, 15, 20, 25, 30, 40, or 50 non-hydrogen atoms. In other embodiments, one or both of $R_3$ and $R_4$ are or include at least one biologically related group, such as an amino acid, dipeptide, tripeptide, oligopeptide, polypeptide (e.g., protein, including an enzyme, antibody, or receptor), nucleobase, nucleoside, nucleotide, dinucleotide, oligonucleotide, polynucleotide, monosaccharide, disaccharide, oligosaccharide, polysaccharide, biotin, avidin, streptavidin, or ligand, any of which may be a small molecule, or a macromolecule containing hundreds of non-hydrogen atoms. In yet other embodiments, one or both of R₃ and R₄ are or include at least one monocyclic unsaturated (or aromatic) ring, which may be a carbomonocyclic unsaturated ring (e.g., benzene, cyclohexene, or cyclopentadiene ring) or a heteromonocyclic unsaturated ring (e.g., o-, m-, or p-pyridine, pyrazine, or pyrimidine ring). In some embodiments, one or both of R₃ and R₄ contribute to the modulation of Sirt2 or provide an important function when the modulating compound is administered to a subject, e.g., R₃ and/or R₄ may make the modulator more bioavailable, function to target Sirt2 more effectively, or function as an adjuvant drug moiety.

In other embodiments of Formula (1), R₄ may be an amino group —NRR', wherein R is typically a hydrocarbon group having up to one, two, three, four, five, or six carbon atoms, and R' is typically a hydrogen atom or a hydrocarbon group having up to one, two, three, four, five, or six carbon atoms, wherein the hydrocarbon groups may or may not be substituted with one or more heteroatoms or heteroatom groups, such as —OH, —OR, —NHR, —NRR'. Some particular examples of such groups for R₄ include —NH₂, —NH(CH₃), —N(CH₃)₂, —NH(CH₂CH₃), —NH(CH₂CH₂OH), —NH(CH₂CH₂OCH₃), —NH(CH₂CH₂NH₂), —NH(CH₂CH₂NH(CH₃), and —NH(CH₂CH₂N(CH₃)₂).

In different embodiments under Formula (1), R₁ is a hydrocarbon group, or more specifically, a straight-chained or branched alkyl group, possessing precisely or at least five, six, seven, eight, nine, ten, eleven, twelve, thirteen, fourteen, fifteen, sixteen, seventeen, eighteen, nineteen, or twenty carbon atoms, or a number of carbon atoms within a range bounded by any two of the foregoing number of carbon atoms (for example, a carbon number in the range of 5-20, 5-18, 5-16, 5-14, 5-12, 5-10, 5-8, 6-20, 6-18, 6-16, 6-14, 6-12, 6-10, 6-8, 7-20, 7-18, 7-16, 7-14, 7-12, 7-10, 8-20, 8-18, 8-16, 8-14, 8-12, 9-20, 9-18, 9-16, 9-14, 9-12, 10-20, 10-18, 10-16, 10-14, 10-12, 11-20, 11-18, 11-16, 11-14, 12-20, 12-18, 12-16, 12-14, 13-20, 13-18, 13-16, 14-20, 14-18, or 14-16 carbon atoms).

In one set of embodiments under Formula (1), the hydrocarbon group R₁ is composed of only carbon and hydrogen atoms. In another set of embodiments, the hydrocarbon group R₁ is composed of carbon and hydrogen atoms, wherein one or more hydrogen atoms may be substituted by one or more fluoro (F) atoms. In another set of embodiments, the hydrocarbon group R₁ is composed of carbon and hydrogen atoms, and optionally one or more fluoro atoms, along with one heteroatom selected from O, N, and S that either interrupts a carbon-carbon bond of the hydrocarbon group R₁ or replaces a carbon atom (i.e., a methylene or methine group) of the hydrocarbon group R₁, except that the heteroatom is not included as an OH, SH, or NH₂ group, or any charged group, such as alkoxide, sulfide, carboxylate, or ammonium groups, since these types of groups would render the acyl portion too hydrophilic (i.e., not sufficiently hydrophobic). The result can be, for example, an ether (R—O—R), thioether (R—S—R), secondary amine (R—NH—R), or tertiary amine (R—NR—R) in R₁, wherein the R groups in each case are independently selected. In some embodiments, the hydrocarbon group R₁ is selected from or includes one or more of: straight-chained or branched alkyl, alkenyl, or alkynyl, which may include or exclude one or more heteroatoms; cycloalkyl; aromatic ring; heterocycloalkyl; heteroaromatic; or a hydrocarbon group that includes any one or more of the foregoing substituent classes, such as an alkyl-aromatic, alkyl-heterocyclic, or alkyl-heteroaromatic group. When a heteroatom replaces a carbon atom, the possibility is included that the heteroatom is attached to the carbon of C(=S), i.e., as C(=S)—O—R₁, C(=S)—S—R₁, C(=S)—NH—R₁, or C(=S)—NR—R₁. In some embodiments, one or more of the foregoing possibilities are excluded.

In particular embodiments of Formula (1), the modulators considered herein have the following chemical structure:

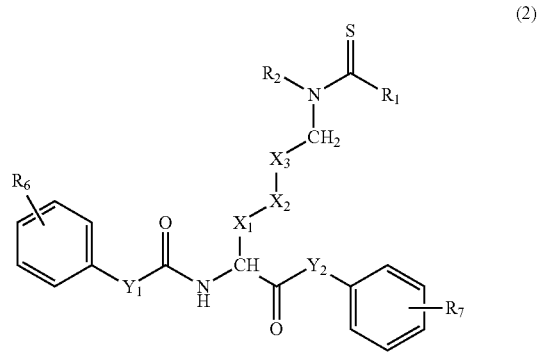

(2)

In Formula (2), the groups R₁, R₂, X₁, X₂, and X₃ are as described above under Formula (1). The groups R₆ and R₇ are independently selected from hydrogen atom, unsubstituted hydrocarbon groups having up to one, two, three, four, five, or six carbon atoms, alkoxy groups —OR (e.g., —OCH₃, —OCH₂CH₃, or —OCH(CH₃)₂), amide groups —NR'C(O)R or —C(O)NR'R (e.g., —NHC(O)CH₃, —N(CH₃)C(O)CH₃, —C(O)NH(CH₃), or —C(O)N(CH₃)₂), ketone groups —C(O)R (e.g., —C(O)CH₃, —C(O)CH₂CH₃, or —C(O)CH(CH₃)₂), ester groups —C(O)OR or —OC(O)R (e.g., —C(O)OCH₃, —C(O)OCH₂CH₃, —OC(O)CH₃, or —OC(O)CH₂CH₃), carbamate groups —OC(O)NR'R or —NR'C(O)OR (e.g., —OC(O)NH(CH₃), —OC(O)N(CH₃)₂, —NHC(O)OCH₃, or —N(CH₃)C(O)CH₃), and urea groups —NR'C(O)NRR' (e.g., —NHC(O)NH(CH₃) or —N(CH₃)C(O)NH(CH₃)), wherein R is a hydrocarbon group having up to one, two, three, four, five, or six carbon atoms, and R' is a hydrogen atom or a hydrocarbon group having up to one, two, three, four, five, or six carbon atoms. The linking moieties Y₁ and Y₂ are independently selected from —O—, —NR₅—, and —S— groups.

In another aspect, the invention is directed to a pharmaceutical composition that includes one or more of the Sirt2-modulating compounds described above dispersed in one or more physiologically acceptable carriers or excipients. The pharmaceutical composition is useful in treating or preventing a disorder whose etiology or expression is dependent on Sirt2 deacylase activity. The phrase "pharmaceutically acceptable excipient" or "pharmaceutically acceptable carrier", as used herein, refers to a pharmaceutically acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and physiologically safe to the subject.

The Sirt2-modulating compound in the pharmaceutical composition can also be a physiologically acceptable salt or solvate of any of the modulator compounds described above. Acceptable salts and solvates can be made by any of the techniques known in the art. As known in the art, a salt can be produced by reacting a basic portion (e.g., amino) of the active compound with a Bronsted acid, such as HCl or H₂SO₄, or with a Lewis acid, such as CH₃Br. If desired, the initially introduced anion or cation can be exchanged with another anion or cation. As also known in the art, a solvate can be produced by dissolving or otherwise treating the active compound with a solvent under conditions where one, two, or more solvent molecules remain associated with each molecule of the active ingredient.

The pharmaceutical composition can also include one or more stabilizers, surfactants, salts, buffering agents, additives, or a combination thereof. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted and buffered.

Pharmaceutical compositions (including cosmetic preparations) may comprise from about 0.00001 to 100%, such as from 0.001 to 10% or from 0.1% to 5% by weight of one or more Sirt2-modulating compounds described herein. In certain topical formulations, the active agent is present in an amount in the range of approximately 0.25 wt % to 75 wt % of the formulation, or in the range of approximately 0.25 wt % to 30 wt % of the formulation, or in the range of approximately 0.5 wt % to 15 wt % of the formulation, or in the range of approximately 1.0 wt % to 10 wt % of the formulation.

In another aspect, the invention is directed to methods for treating or preventing a disorder whose etiology or expression is dependent on Sirt2 deacylase activity. The methods include administering to a subject a Sirt2 modulator in a pharmaceutically effective amount, i.e., an amount that treats or prevents the disorder in a desired manner.

In one set of embodiments, the disorder is cancer. The cancer can be located in any part of the body. Some examples of applicable body parts containing cancer cells include the breasts, lungs, stomach, intestines, prostate, ovaries, cervix, pancreas, kidney, liver, skin, lymphs, bones, bladder, uterus, colon, rectum, or brain. The cancer or neoplasm can also include the presence of one or more carcinomas, sarcomas, lymphomas, blastomas, or teratomas (germ cell tumors). The cancer may also be a form of leukemia.

In another set of embodiments, the disorder is a neurodegenerative disease, which generally refers to a disease that manifests as the progressive loss of neuronal function and structure. The neurodegenerative disease can be, for example, Parkinson's, Alzheimer's, or Huntington's Disease, amyotrophic lateral sclerosis (ALS), peripheral neuropathies, and other conditions characterized by damage, necrosis or loss of neurons, including for example central, peripheral, or motor neurons.

As is well known in the art, the dosage of the active ingredient(s) depends on such factors as the disorder or condition being treated, the extent of the disorder or condition, the method of administration, size of the patient, and potential side effects. In different embodiments, depending on these and other factors, a suitable dosage of the Sirt2 modulator and/or other active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

In certain embodiments, the Sirt2-modulating compounds described herein may be taken alone, while in other embodiments they are taken in combination with one or more other compounds that may or may not also function to modulate Sirt2 or favorably augment or modify the activity of the Sirt2-modulating modulating compound. In one embodiment, a mixture of two or more Sirt2-modulating modulating compounds may be administered to a subject in need thereof. In another embodiment, one or more Sirt2-modulating compounds may be administered with one or more therapeutic agents for the treatment or prevention of a disorder whose etiology or expression is dependent on Sirt2 deacylase activity. In some embodiments, the one or more therapeutic agents are administered at the same time as the Sirt2-modulating compound (e.g., as a pharmaceutical composition containing the one or more therapeutic agents and Sirt2-modulating compound), while in another embodiment, the one or more therapeutic agents are administered separately from the Sirt2-modulating compound. When using separate formulations, the Sirt2-modulating compound may be administered at the same time, prior to, subsequent to, or intermittently or staggered with the administration of another therapeutic agent.

Any of the Sirt2-modulating compounds described herein can be made or modified to have improved properties for administration to a mammalian subject, e.g., to improve stability, cell penetrating ability, longer lifetime, and the like. For example, to enhance cell permeability of the substrate, the modulator can include a peptide chain containing a string of multiple amino acids, such as 8-10 arginine or chemically similar residues, or a polyalkyleneoxide chain, such as a polyethylene glycol (PEG) chain having 2, 3, 4, 5, 6, 7, 8, 9, 10, or a higher number of ethylene oxide units (e.g., on the $R_3$, $R_4$, $R_6$, or $R_7$ groups).

Sirt2-modulating compounds and their physiologically acceptable salts and solvates may be administered (and suitably formulated therefore) by, for example, injection (e.g. SubQ, IM, IP, IV), inhalation or insufflation (either through the mouth or the nose) or oral, buccal, sublingual, transdermal, nasal, parenteral or rectal administration. In one embodiment, a Sirt2-modulating compound may be administered locally, at the site where the target cells are present, i.e., in a specific tissue, organ, or fluid (e.g., blood, cerebrospinal fluid, etc.). Sirt2-modulating compounds can be formulated for a variety of modes of administration, including systemic, topical, or localized administration. Techniques of administration and the design of formulations are well known in the art, such as described in, for example, Remington's Pharmaceutical Sciences, Meade Publishing Co., Easton, Pa.

Toxicity and therapeutic efficacy of Sirt2-modulating compounds can be determined by standard pharmaceutical procedures in cell cultures or experimental animals. The $LD_{50}$ is the dose lethal to 50% of the population. The dose ratio between toxic and therapeutic effects ($LD_{50}/ED_{50}$) is the therapeutic index. Sirt2-modulating compounds that exhibit large therapeutic indexes are preferred. While Sirt2-modulating compounds that exhibit toxic side effects may be used, it is preferable to use a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

In some embodiments, the Sirt2 inhibitor is a selective inhibitor of Sirt2. Generally, by being a selective inhibitor, the Sirt2 inhibitor exhibits an $IC_{50}$ value against Sirt2 that is lower than one or more (or all) other human sirtuins, such as Sirts 1, 3, 4, 5, and 6. For example, the selective Sirt2 inhibitor may exhibit an $IC_{50}$ of up to or less than 50, 40, 30, 20, 10, 5, 2, or 1 µM, while the $IC_{50}$ of one or more (or all) other human sirtuins are greater than any of the foregoing values, or more particularly greater than 50, 60, 70, 80, 90, or 100 µM.

In another aspect, the instant disclosure is directed to an assay method for identifying a modulator of Sirt2 deacylase (specifically, deacetylase) activity. In a particular embodiment, the method is practiced in a high throughput screening mode.

In a first part of the assay method, an acylated substrate (i.e., "substrate") that can be deacylated by Sirt2 (e.g., by substantially mimicking an acylated lysine residue) is contacted with Sirt2 in the presence of a candidate compound. In order for the acylated substrate to be effective, the acyl group of the acyl-lysine moiety (i.e., "acyl-lysine mimicking portion") of the substrate is selected as one that is known to be efficiently deacylated by Sirt2, as found by any suitable experimental protocol that confirms detectable activity of Sirt2 for a particular substrate, as generally known in the art. Typically, the acyl moiety of the substrate contains an alkyl group having at least one, two, or three carbon atoms. Other structural features aside from the acyl-lysine moiety (e.g., those groups attached to the amino or carboxy terminus of the lysine moiety, or a particular peptide sequence) may be suitably adjusted to provide for a more effective substrate if any such additional features are found to have a significant impact on the level of deacylation activity.

The lysine moiety of the substrate may be derivatized or modified in any suitable manner while preserving its basic amino acid structure. In particular, the side-chain ε-aminobutyl group of the lysine moiety can be modified. For example, the lysine moiety can be of the form —NH—CH(R")—C(O)—, where R" is a side-chain, which can be an alkyl or alkenyl chain of, for example, one, two, three, four, five, six, seven, eight, nine, or ten carbon atoms. The acyl group and R" may independently also include or exclude one or more heteroatoms selected from N, O, and S, wherein the heteroatom is either inserted between two carbon atoms or replaces a carbon atom (or methylene group), or is in the form of a heteroatom group, such as C(O). In some embodiments, the heteroatom is not included as an OH, SH, or $NH_2$ group, and one or more hydrogen atoms in the acyl group or R" may or may not be replaced with fluoro atoms. Moreover, if the lysine moiety is not part of an oligopeptide or polypeptide structure, the backbone NH (NH terminus) can be attached to a hydrocarbon group (R), or the hydrogen atom of NH substituted with a hydrocarbon group (R), and/or the backbone C(O) can be attached to a hydrocarbon group (R), or a group —OR, or a group —SR, or a group —NHR, or a group —$NR_2$, wherein each R group is independently selected.

The substrate is linked to an indicator moiety. In embodiments where the substrate has a structure substantially similar to any of the structures shown in Formulas (1) or (2), at least one indicator moiety is included in any generic substituent shown in these formulas. The indicator can be, for example, one or more of the groups selected from $R_3$, $R_4$, $R_6$, and $R_7$, or alternatively, an indicator moiety may be incorporated into any one or more of said groups. The linkage is a covalent linkage that can be severed by a cleavage agent only after the acyl group on the lysine is removed. In particular embodiments, the covalent linkage is an amide bond formed between the carboxyl terminus of the lysine moiety and an amino group of the indicator compound. The indicator moiety is preferably not linked to the acyl portion of the substrate, since this would likely obviate the very mechanism described herein for generating a signal. When the substrate is contacted with Sirt2 under conditions for Sirt2 to deacylate the substrate, the removal of the acyl group permits the cleavage agent to cleave the bond between lysine and indicator moiety, thereby releasing the indicator moiety. Release of the indicator moiety results in the generation of a detectable signal. In particular embodiments, the acyl lysine moiety is linked by a peptide bond to at least one other amino acid residue, and the indicator moiety is linked to the lysine bearing the acyl group (particularly if the lysine bearing the acyl group is at a terminal end) or linked to another amino acid, which may be another lysine that is or is not also acylated, particularly if the lysine bearing the acyl group is interiorized, i.e., not at a terminal end.

The cleavage agent can be any substance that can cleave a peptide bond between specific amino acid residues (i.e., the proteolytic cleavage pattern), but incapable of cleaving the peptide bond if an acylated lysine is present. According to one embodiment, a cleavage agent is a proteolytic enzyme, i.e., an enzyme that hydrolyzes a peptide bond (also referred to as a peptidase). Examples of proteolytic enzymes that can function as a cleavage agent include, but are not limited to trypsin, calpain, lysylendopeptidase, endoproteinase Lys-C, metalloendopeptidase, plasmin, carboxypeptidase, chymotrypsin, V8 protease, pepsin, papain, subtilisin, thrombin, elastase, gluc-C, endo lys-C or proteinase K, caspase-1, caspase-2, caspase-3, caspase-4, caspase-5, caspase-6, caspase-7, caspase-8, MetAP-2, adenovirus protease, HIV protease, and the like.

In a specific embodiment, the cleavage agent is trypsin. Trypsin will cleave peptides attached to the carboxy terminus of the lysine residue of the substrate. Another suitable cleavage agent is pepsin, which hydrolyzes peptide bonds on the amino termini of phenylalanine, tryptophan, and tyrosine residues; thus, pepsin will cleave a substrate peptide between a lysine residue and an adjacent phenylalanine, tryptophan, or tyrosine residue.

The indicator moiety is any molecule that is detectable once cleaved from the substrate. In one embodiment, the indicator moiety is a fluorophore. Some common fluorophores include fluorescein isothiocyanate (FITC), derivatives of rhodamine (TRITC), coumarin, pyrene, cyanine, maleimide derivative dyes, CF dyes, the FluoProbes dyes, the DyLight Fluors, the Oyester dyes, the Atto dyes, the HiLyte Fluors, luciferins, and the Alexa Fluors. Luciferins, such as firefly luciferin, can emit light when incubated with firefly luciferase and ATP. In particular embodiments, the indicator moiety is an aminocoumarin fluorophore, or more specifically, an aminomethylcoumarin fluorophore, such as 7-amino-4-methylcoumarin (AMC).

In some embodiments, fluorescence intensity or emission wavelength of the fluorophore is dependent on the presence or absence of a linkage between the fluorophore and the substrate. The change in fluorescence intensity or emission wavelength of the fluorophore (i.e., as compared before and after cleavage from the substrate) is typically measured with a fluorescence spectrophotometer.

In other embodiments, the fluorophore attached to the substrate does not necessarily change in fluorescence intensity or emission wavelength depending on the presence or absence of a linkage between the fluorophore and the substrate, but a detectable signal is instead provided by also labeling the substrate with a quenching group. For example, the fluorophore can be attached to the carboxyl terminus of the acylated lysine, while the quenching group can be attached to a different amino acid in a peptide chain or other portion of the molecular structure containing the acylated lysine. Prior to cleavage of the fluorophore or quenching group, the fluorescence intensity of these substrates is low due to the close proximity of the quenching group to the fluorophore. After cleavage of either the fluorophore or quenching group from the substrate, the fluorescence intensity is enhanced. This allows measurement of the quantity of the cleaved substrate peptide. Examples of quenching groups suitable for use herein include DNP, Black Hole Quencher™ moieties, and DABCYL. In some embodiments, the quencher may also be a fluorophore.

In some embodiments, the substrate contains a donor-acceptor pair of fluorophores, as commonly used in fluorescence energy transfer (FRET) experiments. Prior to the cleavage of either the donor or acceptor fluorophores, the donor and acceptor fluorophores are in close enough proximity for energy transfer between the donor and acceptor, where such energy transfer can be measured by FRET. One fluorophore can be linked, for example, to the carboxyl terminus of the acylated lysine, and the other member of the donor-acceptor pair placed in close proximity, e.g., attached to another portion of the substrate, such as another amino acid residue of the substrate, or on another portion of the lysine residue, such as on the lysine side chain. When one of the fluorophores of the pair is detached, the FRET signal intensity is significantly diminished, which can be correlated with an activity level for Sirt2.

The candidate compound can be any molecule or macromolecule (e.g., a protein, polynucleotide, or polysaccharide) being tested for its ability to inhibit, activate, or otherwise modulate Sirt2 deacylase activities. In particular embodiments, the candidate compound contains a hydrophobic acyl-lysine mimicking portion, as described above for the substrate, except that the candidate compound is not required to include an indicator moiety (or excludes an indicator moiety). Without being bound by any theory, an effective candidate compound is believed to form a stalled covalent intermediate with Sirt2. Therefore, any structural features that can encourage this interaction with Sirt2 may be included in the candidate compound in an effort to make the candidate compound a more effective modulator. In another embodiment, the candidate compound is a small molecule. A "small molecule" refers to small organic compounds, such as heterocycles, peptides, saccharides, steroids, and the like. The small molecule modulators preferably have a molecular weight of less than or up to about 5000, 3000, 1500, 1000, 800, or 500 Daltons. The candidate compounds may be modified to enhance, for example, efficacy, stability, or pharmaceutical compatibility. In other embodiments, the candidate compound is a compound having a structure within the scope of Formula (1) or (2).

After cleavage of the indicator moiety in the acyl substrate, the signal intensity generated by the cleavage reaction is detected. By methods known in the art for correlating a signal intensity with enzymatic activity, the signal intensity generated by the cleavage reaction is correlated with Sirt2 deacylase activity. The observed deacylase activity, which occurs in the presence of the candidate compound, is compared with deacylase activity of Sirt2 under the same or substantially same conditions except in the absence of the candidate compound (i.e., the control deacylase activity). The control deacylase activity value may be obtained by performing a separate experiment in which the acylated substrate is contacted with Sirt2, in the absence of a candidate compound, under conditions for Sirt2 to deacylate the substrate, contacting the deacylated substrate with a cleavage agent, and observing a signal intensity. The experiment for determining the control deacylase activity value may be included as another step of the instant method conducted directly prior to or after the above-described method that includes the candidate compound. Alternatively, the control deacylase activity value may already be known from a previous experiment, and thus, may not need to be re-established in the above method.

If no difference is found between the control deacylase activity value and the deacylase activity value observed in the presence of the candidate compound, it can be concluded that the candidate compound is not a modulator of Sirt2. Conversely, if a difference is found between the control deacylase activity value and the deacylase activity value observed in the presence of the candidate compound, it can be concluded that the candidate compound is a modulator of Sirt2. A candidate compound is identified as a Sirt2 inhibitor when there is a decrease in Sirt2 deacylase activity in the presence of the candidate compound, relative to Sirt2 deacylase activity in the absence of the candidate compound. A candidate compound is identified as a Sirt2 activator when there is an increase in Sirt2 deacylase activity in the presence of the candidate compound, relative to Sirt2 deacylase activity in the absence of the candidate compound.

To perform an assay for detecting Sirt2 activity, a sample containing Sirt2 is first brought into contact with a suitable substrate described herein and incubated under appropriate conditions. The term "sample" refers to any sample of interest that contains purified, partially purified, or unpurified Sirt2, and can be a lysate from cells or tissues, or a preparation of Sirt2 protein (purified from cells or tissues or a recombinant expression system). Following the incubation period between a Sirt2 sample and a substrate, a cleavage agent is added to the reaction along with an appropriate reaction buffer. Following this second incubation period, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt2 activity. Alternatively, the cleavage agent is present at the time the acylated substrate is in the presence of Sirt2 and the candidate compound, and thus, a second step is not needed for the cleavage reaction.

In some embodiments, the assays are performed in a microplate format. For example, a substrate peptide can be added to a reaction buffer, and the solution poured into wells of a microplate for fluorometry, and the plate then incubated. If the effect of a candidate compound is to be observed, the candidate compound can be included with the substrate. Next, an aliquot of a Sirt2 sample is added to each well, and subjected to deacylation for a given length of time. Subsequently or at the same time, an aliquot of proteolytic enzyme and an appropriate reaction buffer is added to each well, and then the fluorescence intensity of the solution is measured periodically, using a fluorescence microplate reader.

The assays can be miniaturized and automated for high-throughput analysis. The assays can also be performed in one or more separate containers; however, one of the benefits of the disclosed assays is the ability of the assays to be carried out in a single container, such as a microplate well, which allows for ease of use and automation. The substrate may optionally be immobilized on a solid material, such as by biotin-streptavidin linkage, in situations where such immobilization is desired.

Another assay provided herein is a liquid chromatography-mass spectrometry (LCMS) assay. In this assay, Sirt2 activity is identified by determining the amounts of the substrate peptide and product peptide following contact with Sirt2. The liquid chromatography (LC), particularly HPLC, functions to separate substrate from product. The quantification can be achieved by using the area of ultraviolet light absorption (such as at 215 nm or 280 nm) for the product peak and substrate peak on the LC chromatogram, or by using the ion intensity of the product ion and substrate ion in the mass spectrometry. Comparison of the amount of substrate (e.g., acylated peptide) to product (i.e., deacylated peptide) correlates with the amount of Sirt2 activity on the substrate. In this assay, an increase in the amount of product indicates Sirt2 activity, and little or no product indicates little or no Sirt2 activity.

Using a mass spectrometry assay, a candidate compound can be identified as a Sirt2 inhibitor or activator as follows. A candidate compound is identified as a Sirt2 inhibitor when there is a decrease in product (e.g., deacylated peptide) produced in the presence of the candidate compound relative to product produced in the absence of the candidate compound. A candidate compound is identified as a Sirt2 activator when there is an increase in product (e.g., deacylated peptide) produced in the presence of the candidate compound relative to product produced in the absence of the candidate compound. Preferably, in order for the candidate compound to be considered a modulator, the difference in activity between the presence and absence of the candidate compound should be at least, for example, 20%, 30%, 40%, 50%, 60%, 70%, 80%, 90%, 100%, 200%, 300%, 400%, 500% or greater.

In some embodiments, to avoid shortage of the substrate relative to the predicted Sirt2 enzyme activity, an excess amount of the substrate is used in the assay. Specifically, in order to determine the Sirt2 activity in a general biological sample, such as cell nuclear extract, the concentration of the substrate to be used in the reaction is typically 1 to 200 µM, or more particularly, 20 to 50 µM. The concentration of the cleavage agent can also be adjusted depending on the quantity of substrate used. Typically, the amount of the cleavage agent is adjusted according to the predicted quantity of the generated substrate peptide so as to realize enough cleavage of the substrate peptide under a given condition. In particular embodiments, when substrate at a concentration of about 0.01 to 1 mM is used in the reaction, the quantity of trypsin to be used can be, for example, 0.2 to 5 µg per 60 µL reaction, preferably 1 to 2 µg per 60 µL reaction.

With respect to the first reaction (deacylation by Sirt2), the pH for the reaction can be selected by taking the optimal pH of Sirt2 into consideration. The pH is typically adjusted to a pH of 6.0 to 8.5, or more particularly, a pH of 6.8 to 8.5. The reaction buffer preferably provides the above-mentioned pH. For example, Tris-HCl, HEPES-KOH, and other such buffers may be used in the instant method. More specifically, for example, 20 mM Tris-HCl having a pH of 7.4 can be used. Generally, NAD is a co-substrate required for Sirt2 functioning, and is typically used at about 0.5 mM concentration. Salts and preservatives are generally also included in the reaction solution. For example, 1 mM dithiothreitol (DTT) can be added to the reaction. The first reaction (deacylation by Sirt2) can be incubated at, for example, 35-40° C., for a time of, for example, 2-20 hours. Specific exemplary incubation conditions include, for example, incubating a liquid mixture of a substrate and a Sirt2-containing sample in Tris-HCl buffer (pH 7.4, about 20 mM) containing NAD (about 0.5 mM) and DTT (about 1 mM) for about 4 hours at about 37° C. For the second reaction by a cleavage agent, the cleavage agent is added to the reaction along with an appropriate reaction buffer. For example, trypsin (1 µs) and $CaCl_2$ (1 mM) can be added and the reaction incubated for approximately 3 hours at about 37° C.

Following trypsin incubation, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt2 activity as discussed above.

In some embodiments, the substrate, the candidate compound, or both, have $R_3$ and/or $R_4$, or $R_6$ and/or $R_7$, as amide-linked moieties, typically peptide or peptide-mimicking moieties. In particular embodiments, the amide-linked moieties exclude one or more non-amide linkages or groups, such as thioamide, thiourea, sulfonamide, sulfone, sulfamide, sulfoxide, organoester (i.e., —C(O)O—), organothioester (i.e., —C(S)O—), urea, ether (i.e., R—O—R), thioether (i.e., R—S—R), disulfide, azo, carbamate (i.e., —OC(O)NH—), carbonate (i.e., —OC(O)O—), imine, phosphate, phosphonate, phosphinate, and phosphine oxide linkages or groups. In other particular embodiments, the groups that are excluded are hydrolyzable groups, or groups that would undergo hydrolysis or cleavage when introduced into cellular tissue. In some embodiments, one or more such groups may be included if such hydrolysis is desired, or to endow the molecule with other improved properties, such as an improved targeting ability, biodistribution, or bioavailability.

Methods to synthesize the substrates and candidate (or modulator) compounds described herein are known in the art, and as described in the Examples that follow. For example, the coupling of acyl groups to lysine side chains can be accomplished using well known reaction conditions for the preparation of amides from amines and carboxylic acids. Moreover, the conversion of a carbonyl oxygen atom (i.e., $R_2$ or $R_8$) to a thiocarbonyl can be accomplished by, for example, reaction with Lawensson reagent by methods well known in the art.

The ability of a candidate compound to inhibit Sirt2 activity is typically measured by determining the $IC_{50}$ of the candidate compound. As used herein, "$IC_{50}$" or "half maximal inhibitory concentration" identifies how much of a compound is needed to inhibit activity by half. The $IC_{50}$ of a compound can be determined by constructing a dose-response curve and examining the effect of different concentrations of a compound on reducing or preventing enzymatic activity. $IC_{50}$ values can be calculated for a given inhibitor by determining the concentration needed to inhibit half of the maximum enzymatic activity. The mathematical analysis used for deriving an $IC_{50}$ value is well known in the art.

The ability of a candidate compound to activate Sirt2 activity is measured by determining the $EC_{50}$ of the candidate compound. As used herein, "$EC_{50}$" or "half maximal effective concentration" refers to the concentration of a compound that induces a response halfway between the baseline and maximum. The $EC_{50}$ of a graded dose-response curve therefore represents the concentration of a compound where 50% of its maximal effect is observed. The mathematical analysis used for deriving an $EC_{50}$ value is well known in the art.

The Sirt2 inhibitors of the invention preferably inhibit Sirt2 deacylase activity with an $IC_{50}$ or $EC_{50}$ less than or equal to 1 µM, 2 µM, 5 µM, 10 µM, 20 µM, 30 µM, 40 µM, 50 µM, or 100 µM, or an $IC_{50}$ or $EC_{50}$ value within a range bounded by any two of these values.

In another aspect, the invention is directed to a kit useful for measuring the activity of Sirt2 in a sample, and for screening compounds that inhibit or enhance the Sirt2 activity described above. The kit contains, at minimum, a substrate or substrate precursor that includes an acylated lysine or mimic thereof, as described hereinabove. The kit can also include one or more of the following components: one or more samples of Sirt2; a cleavage agent, as described above; one or more candidate compounds or candidate compound precursors; one or more indicator compounds; a quencher; a buffer; a protein-stabilizing or protein-denaturation component, such as BSA or a polyol, such as sucrose or fructose; and one or more devices for combining reagents and/or testing deacylase activity, such as any of the devices or apparatuses used in performing kinetic measurements for determining enzymatic activity.

Examples have been set forth below for the purpose of illustration and to describe the best mode of the invention at the present time. However, the scope of this invention is not to be in any way limited by the examples set forth herein.

EXAMPLE 1

Synthesis of Selected Thioacyl Inhibitors of Sirt2 (TA, TB, TH, and TM)

Figure 2:
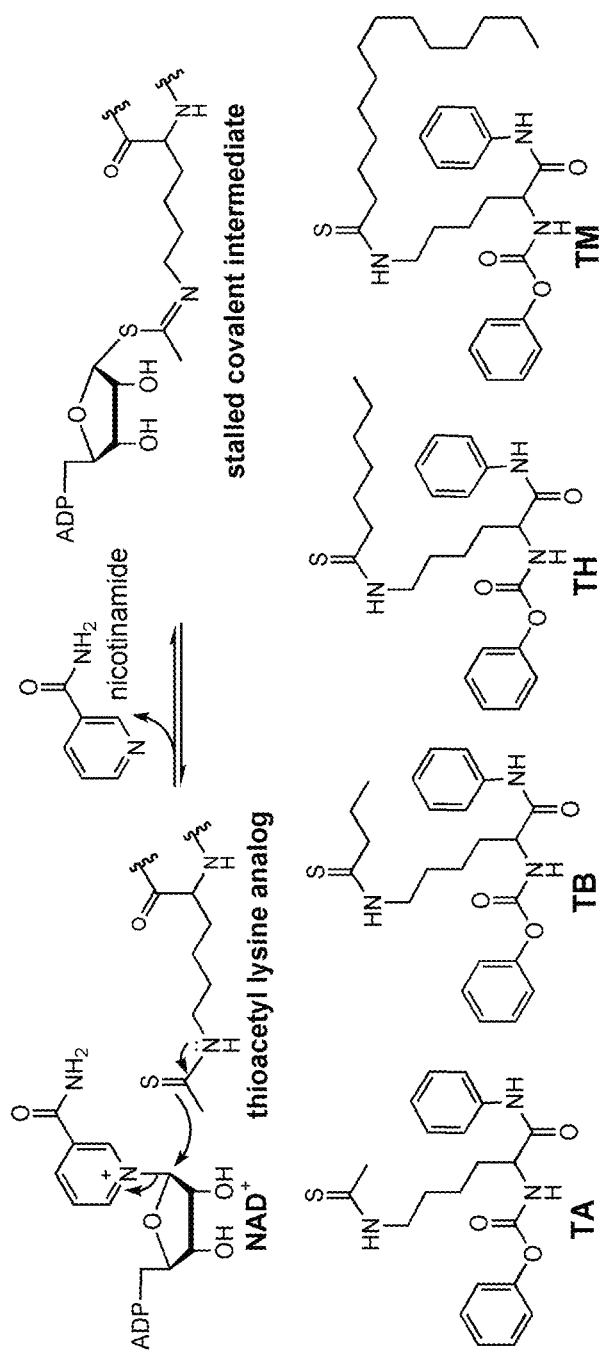
FIG. 2. Top: general schematic depicting the mechanism for the inhibition of sirtuins by thioacetyl lysine compounds. Bottom: structures of some exemplary inhibitors of Sirt2 discovered herein (TA, TB, TH, and TM). The four compounds shown were prepared and tested for their activity against Sirt2.

Four compounds were synthesized and investigated for their Sirt2-inhibiting abilities. The compounds are herein identified as thioacetyl (TA), thiobutyryl (TB), thioheptanoyl (TH), and thiomyristoyl (TM), which correspond to the thioacyl group in these compounds. The structures of the four compounds are shown in FIG. 2 (bottom). FIG. 2 (top) is a general schematic of the mechanism for the inhibition of sirtuins by thioacetyl lysine compounds.

Reagents were obtained in the highest purity available and used as supplied. $^1$HNMR was performed on an INOVA 400 spectrometer. LCMS was performed on a SHIMADZU® LCMS-QP8000α with a Sprite® TARGA C18 column (40× 2.1 mm, 5 µm, Higgins Analytical, Inc., Mountain View, Calif.) monitoring at 215 and 260 nm. Solvents used in LCMS were water with 0.1% formic acid and acetonitrile with 0.1% formic acid. The synthesis of TA is reported in the art (Suzuki, T. et al., *Bioorg. Med. Chem. Lett.* 19, 5670-5672, 2009).

The desired carboxylic acid (e.g., butyric acid, heptanoic acid, or myristic acid, 30 mmol) in anhydrous N,N'-dimethylformamide (DMF, 20 mL) was added to N-hydroxysuccinimide (3.45 g, 30 mmol) with stirring at room temperature. Then N,N'-dicyclohexylcarbodiimide (6.19 g, 30 mmol) in anhydrous DMF (20 mL) was added to the reaction. After stirring for two hours, the reaction mixture was filtered. The filtrate was added to a solution of Cbz-Lys-OH (5.6 g, 20 mmol) with N,N-diisopropylethylamine (DIEA, 5.2 mL, 30 mmol) in anhydrous DMF (50.0 mL) at room temperature (where Cbz=carboxybenzyl, and room temperature (RT) is typically 18-28° C., or more typically, 20-25° C.). The resulting reaction mixture was stirred overnight. Then to the reaction mixture was added 44 mL water and 26 mL 1 M hydrochloric acid (HCl) to adjust pH to about 2 to 3. The mixture was extracted three times with 200 mL ethyl acetate and washed twice with 100 mL brine. The organic layer was dried over anhydrous sodium sulfate. After removal of the solvents under vacuum, the residue containing Cbz-Lys(acyl)-OH was directly used for the next step.

Acetyl chloride (14.2 mL, 200 mmol) was added dropwise to methanol (150 mL) at 0° C. The solution was stirred for 30 minutes at RT. After this time, a solution of 20 mmol of Cbz-Lys(acyl)-OH obtained in the last step in methanol (50 mL) was added and the reaction mixture stirred for a further two hours or overnight. After this time, the solution was concentrated under vacuum and the residue purified through a silica gel column using 20:1 dichloromethane:methanol as eluent to give the product Cbz-Lys(acyl)-OMe in ~95% yield.

Cbz-Lys(acyl)-OMe (20 mmol) was suspended in anhydrous toluene (50 mL). Lawesson's reagent (8.0 g, 20 mmol) was then added to the suspension. The reaction mixture was stirred at 80° C. for two hours under nitrogen (monitored by thin layer chromatography or TLC). After removal of toluene under vacuum, the residue was purified through a silica gel column using 1:4 ethyl acetate:hexane as eluent to give the Cbz-Lys(thioacyl)-OMe product as a white solid in ~90% yield.

Cbz-Lys(thioacyl)-OMe (10 mmol) was dissolved in 1:1 THF:$H_2O$ (100 mL) and the mixture cooled to 0° C. Lithium hydroxide (95.8 g, 40 mmol) was added and the reaction was allowed to warm to room temperature and stirred for three hours (monitored by TLC). The reaction was acidified with 1 M aqueous HCl and extracted with dichloromethane (3×, 150 mL). The combined organic fraction was washed with brine (200 mL), dried over anhydrous sodium sulfate, and concentrated under vacuum. The residue containing the crude product Cbz-Lys(thioacyl)-OH was directly used in the next step without further purification.

To a solution of Cbz-Lys(thioacyl)-OH (10 mmol) and N-methylmorpholine (1.1 mL, 10 mmol) in dry dichloromethane (50 mL) was added isobutylchloroformate (1.3 mL, 10 mmol) dropwise at 0° C. The reaction mixture was stirred for 30 minutes at 0° C. Aniline (1.09 mL, 12 mmol) was added at 0° C. and the reaction mixture stirred overnight at RT. The solvent was removed and the resulting material dissolved in ethyl acetate. The organic layer was washed successively with a saturated solution of sodium bicarbonate, a solution of 0.1N HCl and brine, dried over magnesium sulfate, and concentrated under reduced pressure to afford the expected TB, TH, or TM compound (~90% yield), which was purified by flash chromatography on silica gel with 4:1 hexane:ethyl acetate.

TB $^1$H NMR (400 MHz, $CD_3OD$): δ 7.54-7.50 (m, 2H), 7.33-7.21 (m, 7H), 7.07-7.04 (m, 1H), 5.05 (q, 2H, J=12 Hz), 4.27-4.23 (m, 1H), 3.55 (t, 2H, J=12 Hz) 2.51 (t, 2H, J=8.0 Hz), 1.72-1.68 (m, 8H), 0.86 (t, 3H, J=8.0 Hz). LCMS (ESI) calculated for $C_{24}H_{31}N_3O_3S$ [M+H]$^+$442.2, observed 442.3;

TH $^1$H NMR (400 MHz, $CDCl_3$): δ 8.92 (s, 1H), 8.01 (s, 1H), 7.47-7.06 (m, 10H), 6.12 (s, 1H), 5.09-5.00 (m, 2H), 4.43 (s, 1H), 3.58 (s, 2H), 2.56 (t, 2H, J=8 Hz), 1.87-1.23 (m, 14H), 0.84 (s, 3H). LCMS (ESI) calculated for $C_{27}H_{37}N_3O_3S$ [M+H]$^+$484.3, observed 484.3;

TM $^1$H NMR (400 MHz, $CD_3OD$): δ 7.54-7.52 (m, 2H), 7.36-7.26 (m, 7H), 7.10-7.06 (m, 1H), 5.12-5.04 (m, 2H), 4.23-4.20 (m, 1H), 3.57 (t, 2H, J=8.0 Hz) 2.54 (t, 2H, J=8.0 Hz), 1.84-1.26 (m, 28H), 0.87 (t, 3H, J=8.0 Hz). LCMS (ESI) calculated for $C_{34}H_{51}N_3O_3S$ [M+H]$^+$582.4, observed 582.5.

EXAMPLE 2

Elucidation of Sirt2-Inhibiting Abilities of TA, TB, TH, and TM Inhibitors

Distinct selectivity profiles were found for each of the inhibitors studied. The $IC_{50}$ values (μM) for each of the studied inhibitor compounds are provided in Table 1 below. Different concentrations of TA, TB, TH, or TM were pre-incubated with 1 μM of the sirtuin and 1 mM NAD in 20 mM Tris-HCl buffer (pH 8.0) with 1 mM dithiothreitol (DTT) at 37° C. for 30 minutes. Then 0.05 mM acyl peptides (H3K9Ac for Sirt1, Sirt2 and Sirt3; H3K9Su for Sirt5; H3K9Myr for Sirt6 and Sirt7) were added to initiate the reactions. The total reaction volume iwas 60 mL. Then reactions were incubated at 37° C. for a certain amount of time (2 minutes for Sirt1, 10 minutes for Sirt2 and Sirt5, 30 minutes for Sirt3, and 1 hour for Sirt6 and Sirt7). The reactions were stopped by adding 60 mL of an aqueous solution containing 200 mM HCl and 320 mM acetic acid. After centrifugation to remove precipitated proteins, the supernatant was analyzed by HPLC with a reverse phase C18 column (250×4.6 mm, 90 A, 10 mm, GraceVydac, Southborough, Mass.), with a linear gradient of 0% to 20% B for 10 minutes (1 mL/min). Product quantification was based on the area of absorbance monitored at 215 nm, assuming hydrolysis of the acyl group does not affect the absorbance. All reactions were done in duplicate.

In particular, as shown by Table 1, TB and TH can efficiently inhibit Sirt1, while TH and TM can efficiently inhibit Sirt2. As also shown by the data in Table 1, none of these compounds effectively inhibit Sirt3, Sirt5, or Sirt6. Of particular significance are the $IC_{50}$ values of TM, which shows TM to be a Sirt2-selective inhibitor with >50-fold better efficiency at inhibiting Sirt2 as compared to the other sirtuins tested. This remarkable selectivity for Sirt2 is particularly unexpected. Moreover, as a trend is observed in which selectivity for Sirt2 increases with increasing acyl chain length, there has been provided evidence that inhibitor compounds containing acyl chain lengths greater than that found in TH and less than TM (i.e., above 6 and less than 13 carbon atoms) and acyl chain lengths above that found in TM (e.g., above 13 and up to 16, 17, 18, 19, or 20 carbon atoms) would also show substantial selectivity against Sirt2.

TABLE 1

$IC_{50}$ values (μM) of different compounds for Sirt1, 2, 3, 5, 6, and 7

| | TA | TB | TH | TM |
|---|---|---|---|---|
| Sirt1 | 30 | 2.4 | 0.31 | >205 |
| Sirt2 | 105 | 3.0 | 0.12 | 0.05 |
| Sirt3 | >205 | 113 | 105 | 124 |
| Sirt5 | >205 | >205 | >205 | >205 |
| Sirt6 | >205 | >205 | >205 | >205 |
| Sirt7 | >205 | >205 | >205 | >205 |

EXAMPLE 3

In Vitro Cancer Inhibition Abilities of TA, TB, TH, and TM Inhibitors

Next, the ability of these inhibiting compounds to inhibit cancer cell proliferation was tested. MCF-7 and MDA-MB-231 cells (ATCC) were both maintained in RPMI 1640 media (Invitrogen®) supplemented with 10% heat-inactivated fetal bovine serum (FBS). MCF-10A (ATCC) cells were maintained in Dulbecco's Modified Eagle Medium: Nutrient Mixture F-12 (DMEM/F12) (Invitrogen®) supplemented with 10% horse serum (Invitrogen®).

General Procedure for Soft Agar Assay

The 0.6% agarose type VII (Sigma), 10% FBS and 1% Penicillin-Streptomycin (Invitrogen®) were prepared in RPMI 1640 medium, and added to a six-well culture plate (2 mL/well). The plates were kept at ° C. for 20 minutes to allow the agarose to solidify. Plates were then incubated at 37° C. for 5 minutes before the addition of the 1 mL soft agar/cell solution prepared by mixing 0.3% agarose type VII, 10% FBS, 1% Penicillin-Streptomycin and ~3000 cells in RPMI 1640 medium. Again, the plates were kept at 4° C. for 20 minutes to allow the agarose to solidify. After the plates were incubated at 37° C. for 7 days, 1 mL of RPMI 1640 medium with 0.3% agarose type VII, 10% FBS and 1% Penicillin-Streptomycin was added to the plates and the plates kept at 4° C. for 20 minutes to allow the agarose to solidify. After the plates were incubated at 37° C. for another 7 days, the colony formations were examined under a microscope. All the experiments were duplicated. For testing inhibitors, indicated concentrations of inhibitors in dimethyl sulfoxide (DMSO) or DMSO alone (negative control) were added into the soft agar/cell solution; for testing knock-down cells, indicated knock down cells were added into the soft agar/cell solution.

General Procedure for Low Serum Survival Assay

For MCF-7 and MDA-MB-231 cell lines, ~6000 cells in 2 mL of RPMI 1640 medium with 3% FBS (or in 2 mL DMEM/F12 with 3% horse serum for MCF-10A cell line) were plated into a six-well culture plate. After cells were attached to the plates, indicated concentrations of inhibitors in DMSO or DMSO alone (negative control) were added into the plates. After washing with phosphate buffered saline (PBS), live cell numbers were counted at day 0, day 1, day 3, and day 5. The testing was duplicated.

Figure 3A:
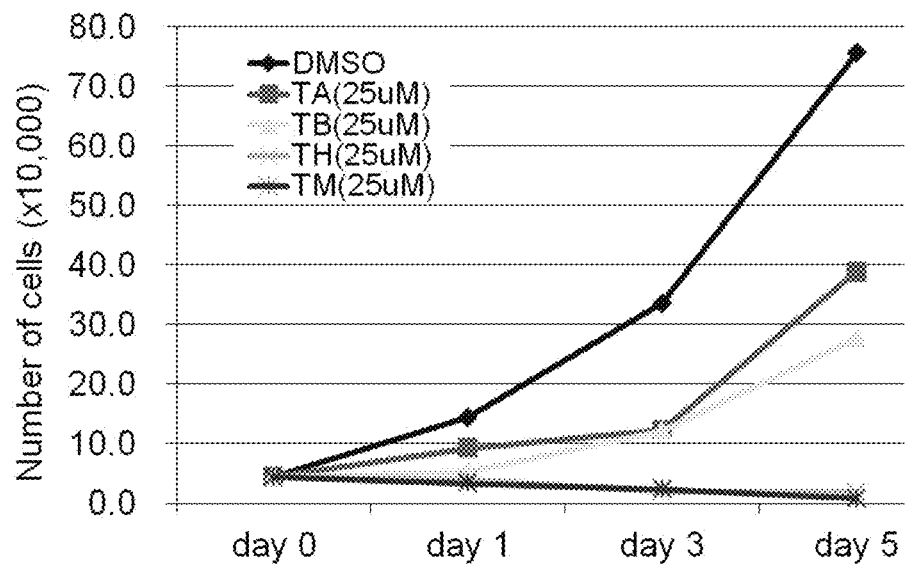
FIGS. 3A, 3B. Graph showing inhibition ability of the four exemplary Sirt2 inhibiting compounds (TA, TB, TH, and TM), with DMSO used as a control, FIG. 3(A). (B) Graph showing inhibition ability of TH and TM (25 μM) against MCF7 cancer cell line and MCF10a normal cell line, FIG. 3(B).
Figure 3B:
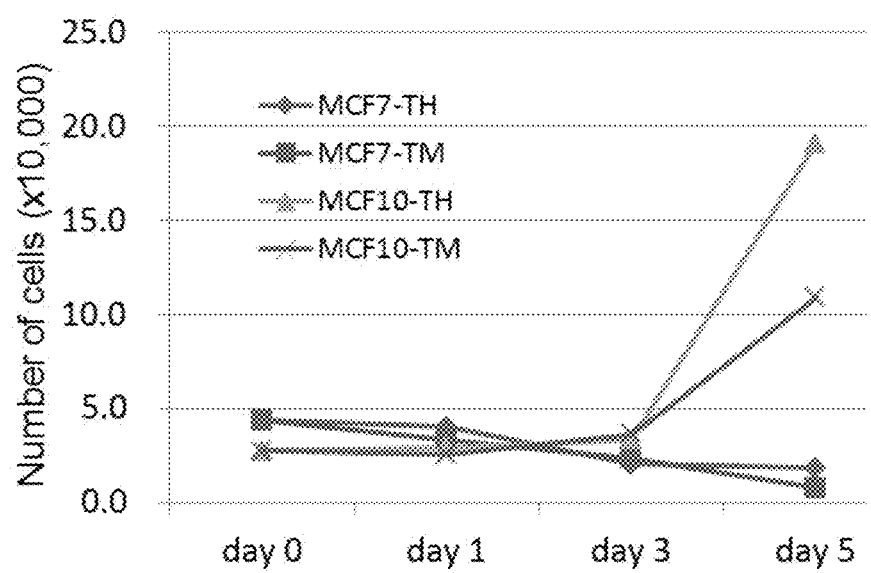

FIG. 3(A) is a graph showing inhibition ability of the four exemplary Sirt2 inhibiting compounds (TA, TB, TH, and TM), with DMSO used as a control. As shown, Sirt2 inhibitors (TH and TM) can effectively inhibit cancer cell proliferation, and TB, which can only effectively inhibit Sirt1, has only minor effect on cancer cell proliferation. FIG. 3(B) is a graph showing inhibition ability of TH and TM (25 μM) against MCF7 breast cancer cell line and MCF10a normal cell line. As shown, TH and TM are more toxic to cancer cells as the effect in MCF 10a (a normal non-tumorigenic human mammary epithelial cell line) is much less than that in the MCF7 cancer cell line. Moreover, as also shown by FIG. 3(B), at a concentration of 25 μM, the Sirt2-selective inhibitor, TM, completely inhibited the proliferation of MCF7 cells. The Sirt1-selective inhibitor, TB, only showed a very modest effect. In contrast, TH, which can inhibit both Sirt1 and Sirt2, is similarly efficient as TM. These data suggest that inhibiting Sirt2, but not Sirt1, can inhibit cancer cell proliferation. Thus, as the Sirt2 inhibitors can effectively inhibit MCF7 cancer cell proliferation, the Sirt2 inhibitors described herein have been shown to be useful in the treatment of cancer, particularly breast cancer.

As also shown by FIGS. 3(A) and 3(B), the growth inhibition/toxicity is selective towards cancer cells, because MCF10a cells, which are considered to be non-cancer cells, can still grow in the presence of 25 μM of TH or TM, which completely inhibited the growth of the cancer cell line MCF7.

Figures 4A, 4B:
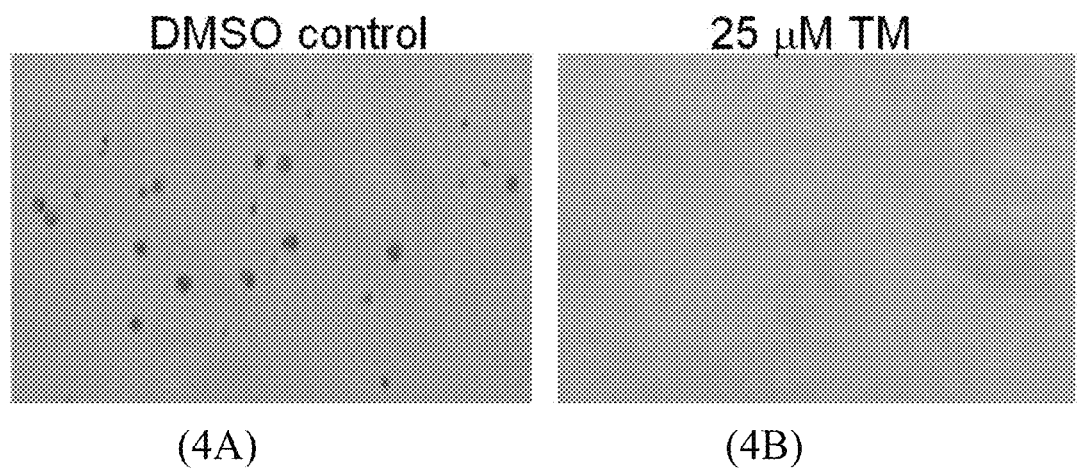
FIGS. 4A, 4B. Micrographs of a soft agar assay, which demonstrates that the Sirt2-specific inhibitor, TM, can inhibit the anchorage-independent growth of TNBC cell line MDA-MB-231.

As shown by the assay micrographs in FIGS. 4(A) and 4(B), it has also herein been found that the Sirt2-specific inhibitor TM at 25 μM concentration can inhibit the anchorage-independent growth of triple negative breast cancer cell line MDA-MB-231. Triple-negative breast cancer lacks estrogen receptor (ER) and progesterone receptor (PR) expression, as well as human epidermal growth factor receptor 2 (HER2) amplification. Triple negative breast cancer is more difficult to treat clinically, and thus, there is an outstanding effort to identify new targets and development of new therapeutic agents. The Sirt2-specific inhibition by TM demonstrates that Sirt2-selective inhibitors can be used in the treatment of triple negative breast cancer.

Figures 5A, 5B, 5C:
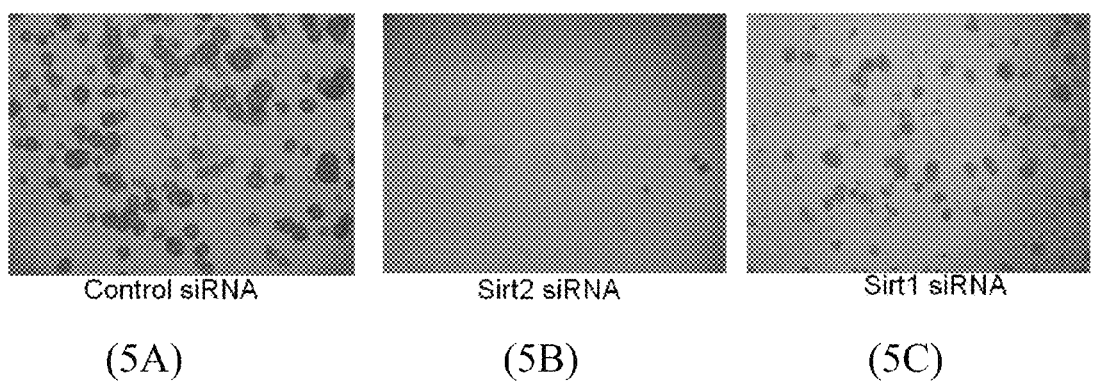
FIGS. 5A-5C. Micrographs of a soft agar assay, which demonstrates that Sirt2 KD, but not Sirt1 KD, can efficiently inhibit colony formation by MCF7 cells.

To validate that inhibiting Sirt2 led to the inhibition of the anchorage-independent growth of cancer cells, another experiment knocked down Sirt1 and Sirt2 with siRNA. As shown by the assay micrographs in FIGS. 5(A), 5(B), and 5(C), Sirt2 KD, but not Sirt1 KD, almost completely inhibited anchorage-independent growth of MCF7 cells. The KD data is in complete agreement with the small molecule inhibition data and suggest that Sirt2 is a new therapeutic target for breast cancer.

While there have been shown and described what are at present considered the preferred embodiments of the invention, those skilled in the art may make various changes and modifications which remain within the scope of the invention defined by the appended claims.

What is claimed is:

1. A compound that modulates Sirt2 activity having the following chemical structure:

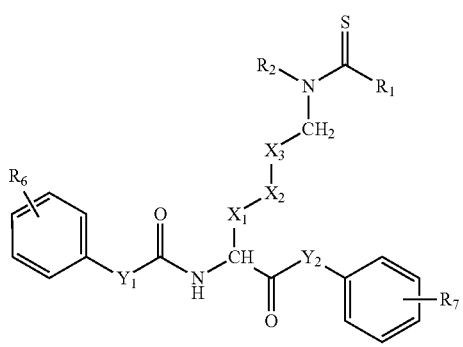

(2)

wherein $R_1$ is a hydrocarbon group having at least five carbon atoms connected by carbon-carbon bonds, wherein said hydrocarbon group optionally includes one heteroatom group selected from —O—, —$NR_5$—, and —S— that interrupts a carbon-carbon bond of said hydrocarbon group, and wherein one or more hydrogen atoms in said hydrocarbon group are optionally replaced with fluoro atoms, wherein $R_5$ is a hydrogen atom or a hydrocarbon group;

$R_2$ is selected from a hydrogen atom or a hydrocarbon group;

$R_6$ and $R_7$ are independently selected from hydrogen atom, unsubstituted hydrocarbon groups having up to six carbon atoms, alkoxy groups —OR, amide groups —NR'C(O)R or —C(O)NR'R, ketone groups —C(O)R, ester groups —C(O)OR or —OC(O)R, carbamate groups —OC(O)NR'R or —NR'C(O)OR, and urea groups —NR'C(O)NR, wherein R is a hydrocarbon group having up to six carbon atoms, and R' is a hydrogen atom or a hydrocarbon group having up to six carbon atoms;

$X_1$, $X_2$, and $X_3$ are independently selected from —$(CH_2)_n$—, —$NR_5$—, —O—, —S—, or a bond, wherein n represents 1, 2, or 3, and at least one of $X_1$, $X_2$, and $X_3$ is a —$CH_2$—group; and $Y_1$ and $Y_2$ are independently selected from —O—, —$NR_5$—, and —S— groups.

2. The compound of claim 1, wherein said hydrocarbon group for $R_1$ has at least five carbon atoms connected by carbon-carbon bonds in the absence of heteroatom interruption, except that one or more hydrogen atoms are optionally replaced with fluoro atoms.

3. The compound of claim 1, wherein said hydrocarbon group for $R_1$ has at least six carbon atoms.

4. The compound of claim 1, wherein said hydrocarbon group for $R_1$ has at least seven carbon atoms.

5. The compound of claim 1, wherein said hydrocarbon group for $R_1$ has at least eight carbon atoms.

6. The compound of claim 1, wherein said hydrocarbon group for $R_1$ has up to twenty carbon atoms.

7. The compound of claim 1, wherein each of $X_1$, $X_2$, and $X_3$ is —$(CH_2)_n$—, wherein n is independently 1, 2, or 3.

8. The compound of claim 1, wherein each of $X_1$, $X_2$, and $X_3$ is —$CH_2$—.

9. The compound of claim 1, wherein $Y_1$ is an —O— atom.

10. The compound of claim 1, wherein $Y_2$ is an —$NR_5$— group.

11. The compound of claim 1, wherein $Y_1$ is an —O— atom and $Y_2$ is an —$NR_5$— group.

12. The compound of claim 1, wherein $R_6$ and $R_7$ are independently selected from hydrogen atom, unsubstituted hydrocarbon groups having up to three carbon atoms, alkoxy groups —OR, amide groups —NR'C(O)R or —C(O)NR'R, ketone groups —C(O)R, ester groups —C(O)OR or —OC(O)R, carbamate groups —OC(O)NR'R or —NR'C(O)OR, and urea groups —NR'C(O)NR, wherein R is a hydrocarbon group having up to three carbon atoms, and R' is a hydrogen atom or a hydrocarbon group having up to three carbon atoms.

13. A method for treating a subject suffering from a neurodegenerative disorder, the method comprising administering to said subject a modulator of Sirt2 according to claim 1 in a pharmaceutically effective amount for treating said neurodegenerative disorder, wherein said neurodegenerative disorder is selected from Parkinson's Disease, Huntington's Disease, and Alzheimer's Disease.

14. The method of claim 13, wherein said neurodegenerative disorder is Parkinson's Disease.

15. The method of claim 13, wherein said modulator of Sirt2 is an inhibitor of Sirt2.

16. The method of claim 15, wherein said inhibitor of Sirt2 is a selective inhibitor of Sirt2.

17. The method of claim 13, wherein the hydrocarbon group for $R_1$ has at least five carbon atoms connected by carbon-carbon bonds in the absence of heteroatom interruption, except that one or more hydrogen atoms are optionally replaced with fluoro atoms.

18. A method for treating a subject suffering from breast cancer, the method comprising administering to said subject a modulator of Sirt2 in a pharmaceutically effective amount for treating said breast cancer, the modulator of Sirt2 having the following chemical structure:

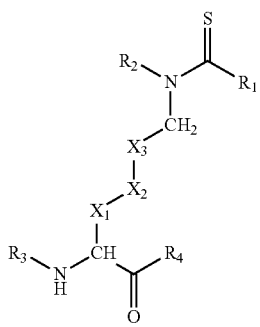

(1)

wherein R₁ is a hydrocarbon group having at least five carbon atoms connected by carbon-carbon bonds, wherein said hydrocarbon group optionally includes one heteroatom group selected from —O—, —NR₅—, and —S— that interrupts a carbon-carbon bond of said hydrocarbon group, and wherein one or more hydrogen atoms in said hydrocarbon group are optionally replaced with fluoro atoms, wherein R₅ is a hydrogen atom or a hydrocarbon group;

R₂ is selected from a hydrogen atom or a hydrocarbon group;

R₃ and R₄ are independently selected from hydrogen atom and hydrocarbon groups R, wherein said hydrocarbon groups R are optionally substituted with one or more heteroatoms; and X₁, X₂, and X₃ are independently selected from —(CH₂)ₙ—, —NR₅—, —O—, —S—, or a bond, wherein n represents 1, 2, or 3, and at least one of X₁, X₂, and X₃ is a —CH₂— group.

19. The method of claim 18, wherein the hydrocarbon group for R₁ has at least five carbon atoms connected by carbon-carbon bonds in the absence of heteroatom interruption, except that one or more hydrogen atoms are optionally replaced with fluoro atoms.

20. The method of claim 18, wherein said modulator of Sirt2 is an inhibitor of Sirt2.

21. The method of claim 20, wherein said inhibitor of Sirt2 is a selective inhibitor of Sirt2.

22. The method of claim 18, wherein said breast cancer is triple negative breast cancer.

23. The method of claim 18, wherein at least one of R₃ and R₄ is comprised of at least one amino acid residue.

24. The method of claim 18, wherein at least one of R₃ and R₄ is comprised of a monocyclic unsaturated ring.

25. The method of claim 18, wherein each of R₃ and R₄ is comprised of a monocyclic unsaturated ring.

26. The method of claim 18, wherein said modulator of Sirt2 has the following chemical structure:

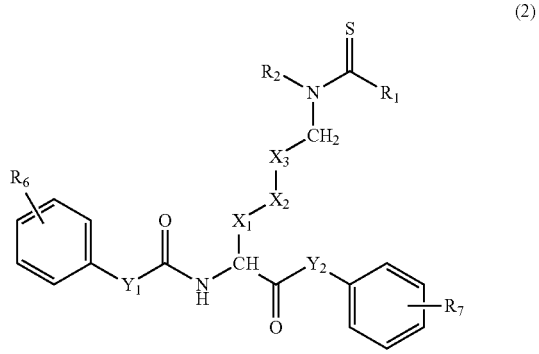

(2)

wherein R₁ is a hydrocarbon group having at least five carbon atoms connected by carbon-carbon bonds, wherein said hydrocarbon group optionally includes one heteroatom group selected from —O—, —NR₅—, and —S— that interrupts a carbon-carbon bond of said hydrocarbon group, and wherein one or more hydrogen atoms in said hydrocarbon group are optionally replaced with fluoro atoms, wherein R₅ is a hydrogen atom or a hydrocarbon group;

R₂ is selected from a hydrogen atom or a hydrocarbon group;

R₆ and R₇ are independently selected from hydrogen atom, unsubstituted hydrocarbon groups having up to six carbon atoms, alkoxy groups —OR, amide groups —NR'C(O)R or —C(O)NR'R, ketone groups —C(O)R, ester groups —C(O)OR or —OC(O)R, carbamate groups —OC(O)NR'R or —NR'C(O)OR, and urea groups —NR'C(O)NR, wherein R is a hydrocarbon group having up to six carbon atoms, and R' is a hydrogen atom or a hydrocarbon group having up to six carbon atoms;

X₁, X₂, and X₃ are independently selected from —(CH₂)ₙ—, —NR₅—, —O—, —S—, or a bond, wherein n represents 1, 2, or 3, and at least one of X₁, X₂, and X₃ is a —CH₂— group; and Y₁ and Y₂ are independently selected from —O—, —NR₅—, and —S— groups.

* * * * *